United States Patent [19]
Roulier et al.

[11] 3,992,111
[45] Nov. 16, 1976

[54] APPARATUS FOR DETECTING DEFECT LOCATIONS AT THE SURFACE OF A MOVING REFLECTING MATERIAL

[75] Inventors: Alfred Roulier, Neuenegg; Walter Kamber, Marly, both of Switzerland

[73] Assignee: Ciba-Geigy AG, Basel, Switzerland

[22] Filed: Jan. 30, 1975

[21] Appl. No.: 545,468

[30] Foreign Application Priority Data
Feb. 1, 1974    Germany............................ 2404972

[52] U.S. Cl................................ 356/200; 250/572; 350/271; 350/274; 356/209
[51] Int. Cl.[2].......................................... G01N 21/32
[58] Field of Search ........... 356/200, 199, 209, 211, 356/188; 350/273, 274; 250/571, 572

[56] References Cited
UNITED STATES PATENTS

| | | | |
|---|---|---|---|
| 1,860,967 | 5/1932 | Tate.................................... | 350/274 |
| 2,208,420 | 7/1940 | Gulliksen............................ | 356/199 |
| 2,246,501 | 6/1941 | Bradner et al...................... | 356/199 |
| 3,052,168 | 9/1962 | Reed................................... | 350/274 |
| 3,202,043 | 8/1965 | Galey et al......................... | 356/200 |
| 3,330,961 | 7/1967 | Juengst et al...................... | 356/200 |
| 3,618,063 | 11/1971 | Johnson et al...................... | 356/200 |
| 3,666,370 | 5/1972 | Seasholtz............................ | 356/200 |

FOREIGN PATENTS OR APPLICATIONS

| | | | |
|---|---|---|---|
| 666,513 | 10/1938 | Germany............................ | 356/211 |
| 880,135 | 10/1961 | United Kingdom................ | 356/200 |

*Primary Examiner*—John K. Corbin
*Assistant Examiner*—Richard A. Rosenberger
*Attorney, Agent, or Firm*—Harry Falber; Karl F. Jorda

[57] ABSTRACT

Apparatus for detecting defect locations at the surface of a moving reflecting material comprising a light source and a first optical system which directs the light thereof successively upon surface regions of the material situated along a line extending essentially transversely to the direction of movement of the material. A photoelectric transducer and a second optical system are provided, the second optical system collecting the light reflected from the individual surface regions at the transducer. An indicator device or mechanism which as a function of the intensity of the light reflected by each surface region produces a signal, especially an optical signal, which is associated with the relevant surface region. According to the invention the light source is a laser light source, the first optical system splits up the laser beam into an essentially two-dimensional parallel bundle of rays, the plane of which intersects the surface of the material to be examined approximately perpendicularly and which grazingly impinges upon the material surface, especially at an angle less than 5°, and that in the path of the rays of the light impinging upon the material there is arranged a movable diaphragm which periodically only frees individual partial regions of the planar bundle of rays.

10 Claims, 3 Drawing Figures

APPARATUS FOR DETECTING DEFECT LOCATIONS AT THE SURFACE OF A MOVING REFLECTING MATERIAL

BACKGROUND OF THE INVENTION

The present invention relates to a new and improved apparatus for detecting flaws or defect locations at the surface of a moved reflecting material.

The apparatus of this development is of the type embodying a light source and a first optical system which directs the light thereof successively upon a surface region of the material located along a line extending essentially transversely with respect to the direction of movement of the material. There is also provided a photoelectric transducer and a second optical system which collects the light reflected from the individual surface regions at the transducer, and an indicator device which as a function of the intensity of the light reflected by each surface region generates a signal, especially an optical signal, which is associated with the relevant surface region. Equipment of this type is particularly employed for the surface control during the fabrication of photographic materials, such as films, paper, etc.

With known apparatuses of this type there is illuminated, through the agency of a movable optical system, in succession partial zones or regions of the material web to be examined (flying-spot-technique), and imaged via a second optical system at a stationary light detector. These prior art apparatuses are relatively complicated and require large optical components which extend over the entire width of the material web and past the same. Since such large optical components are difficult to fabricate and thus expensive the state-of-the-art apparatuses are only suitable for relatively small material web widths.

SUMMARY OF THE INVENTION

Hence, it is a primary object of the present invention to provide an improved construction of apparatus for detecting defect locations at the specular surface of a moving material in a manner not associated with the aforementioned drawbacks and limitations of the state-of-the-art proposals.

Another and more specific object of the invention aims at the provision of an apparatus of the previously mentioned type which is relatively simple in construction and also suitable for use with material webs of relatively large width.

Now in order to implement these and still further objects of the invention which will become more readily apparent as the description proceeds, the invention contemplates that the light source is a laser light source, that the first optical system splits or divides the laser beam into an essentially two-dimensional parallel bundle or beam of rays, the plane of which approximately perpendicularly intersects the surface of the material which is to be examined and which beam of rays grazingly impinges upon the material surface, especially at an angle which is less than 5°. Further, in the path of the rays of the light impinging upon the material there is arranged a movable diaphragm which periodically only frees individual partial regions of the planar bundle of light rays.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
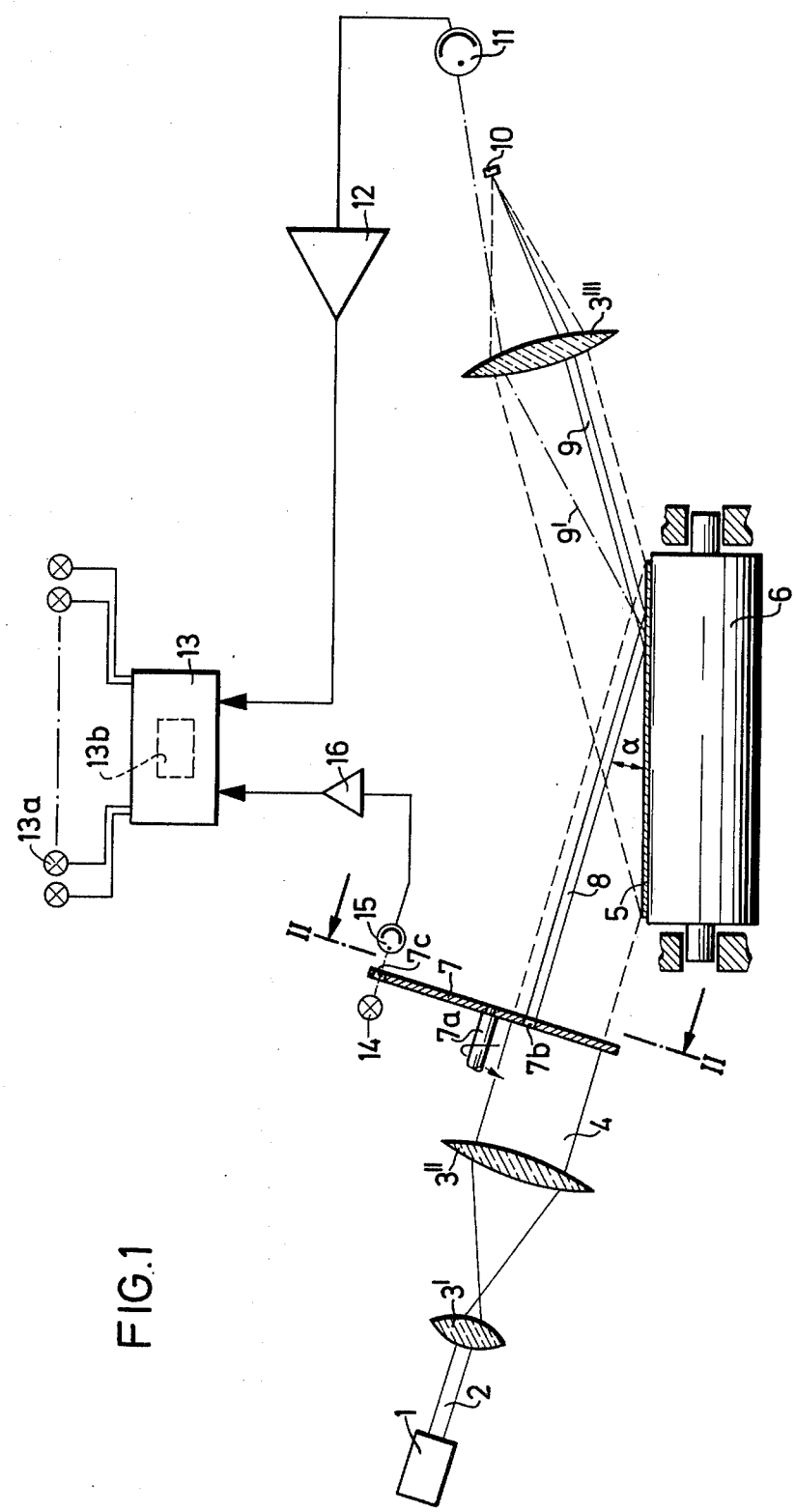
FIG. 1 is a schematic illustration of the apparatus of this development.

Describing now the drawings it is to be understood that only enough of the apparatus structure of this development has been shown in order to preserve clarity in illustration and to provide a detailed understanding of the basic and underlying concepts of the invention. Referring therefore more particularly to FIG. 1, a parallel bundle of light rays 2, emanating from a laser light source 1, is fanned out into an essentially two-dimensional parallel bundle of light rays 4 by means of a system of cylindrical lenses 3' and 3''. The plane of the parallel bundle of light rays 4 is located in the plane of the drawing. The wavelength of the laser light can be in the longwave visible range of the spectrum or in the shortwave infrared range. The thickness of the parallel bundle of light rays perpendicular to its plane amounts to only a few millimeters. The parallel bundle of light rays 4 grazingly impinges at a very flat angle $\alpha$ upon the reflecting or specular surface of a material web 5 which is to be examined or inspected, for instance a web of a photographic film, and at that location is reflected at the same angle. The angle of incidence $\alpha$ preferably amounts to less than 5°. It is to be understood however that in the drawings it has been illustrated to be considerably larger in order to improve the recognizability thereof. The width of the parallel bundle of light rays is dimensioned such that the same, for a given angle of incidence $\alpha$, scans the entire width of the material web, as such has been indicated in FIG. 1 by the broken lines. The material web 5 which is to be examined can be forwardly advanced in its lengthwise direction via rollers 6 and in a direction which is perpendicular to the plane of the drawing.

Figure 2:
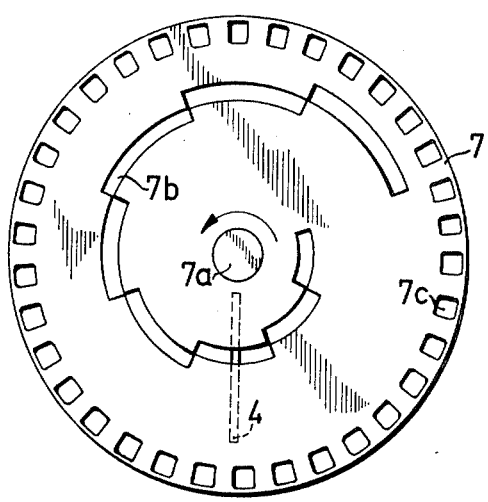
FIG. 2 is a view on an enlarged scale taken along the line II—II of FIG. 1.

In the path of the light rays impinging upon the material web surface there is located a movable diaphragm or light stop 7 which is in the form of a substantially circular disk rotatable about its axis 7a by means of any suitable and therefore not particularly illustrated drive motor. The diaphragm disk 7 has been shown on an enlarged scale in FIG. 2. It possesses a series of arcuate-shaped slots 7b, all of which are concentrically arranged with respect to the axis of the disk and possess the same central angle, i.e. angle at the center of the disk. Their spacing from the disk axis and thus their radii are however different. The rotational axis 7a of the diaphragm disk 7 is located in the plane of the parallel bundle of light rays 4 parallel to the light rays, however externally thereof. The diameter of the disk is dimensioned such that the same can interrupt the bundle of light rays over its entire width. The position of the bundle of light rays 4 with respect to the diaphragm disk 7 has been indicated in FIG. 2 in phantom lines. Depending upon the rotational position of the disk 7, by means of the slots 7b thereof only a narrow partial region or portion 8 of the bundle of light rays 4 is freed, which periodically travels transverse to the direction of spreading or fanning out of the rays and thus in each instance only illuminates a small surface region of the material web which travels periodically to-and-fro transversely with respect to the material web-lengthwise direction. With the illustrated exemplary embodiment the material web 5 is divided into eight such regions corresponding to the number of slots in the diaphragm. Of course, there would be possible a coarser or finer subdivision.

The light 9 reflected by the specular surface of the material web 5 is collected by means of a further optical element or lens 3''' at a non-transparent barrier or obstacle 10. Behind this obstacle 10 there is arranged a photoelectric transducer 11, for instance a phototransistor or the like. Now when the surface of the material web to be examined does not possess any defect locations, then all the light is collected at the obstacle or hinderance 10 and the transducer 11 is not illuminated. On the other hand, in the case of a defect location at the material surface the light rays are reflected at an angle other than α and therefore no longer impinge upon the barrier or obstacle 10, rather are diverted therepast and arrive at the photoelectric transducer 11, as such has been indicated by the phantom-line illustrated light ray 9'. Hence, the photoelectric transducer 11 only then delivers an electrical signal when there is illuminated a defect or flaw location at the surface of the material. This signal is delivered through the agency of an amplifier 12 to an indicator device 13 which possesses a number of control lamps 13a corresponding to the number of slots in the diaphragm disk 7. It will be understood therefore that each control lamp is operatively associated with a certain surface region of the web width.

The diaphragm disk 7 is provided at its outer or marginal edge with holes or apertures 7c which together with a light barrier consisting of a lamp 14 and a photocell 15 controls via an amplifier 16 a system, generally indicated by reference character 13b, contained in the indicator device 13 for determining the rotational position of the diaphragm disk 7. In the indicator device 13 there are correlated the signals emanating from the transducer 11 and the system for detecting the rotational position, that is to say, a signal of the transducer 11 which indicates a defect location is correlated or associated with the momentary rotational position of the diaphragm disk 7 and therefore the location of the defect in a certain surface region on the material web. In the presence of a defect location there is illuminated the corresponding signal lamp 13a associated with each such region. In this way it is possible in a very simple manner to pin-point or localize surface flaws or defects.

Preferably the indicator device 13 is constructed such that the duration of illumination of the signal lamps 13a, upon the presence of a defect location, is just as long as the period or time of the diaphragm movement. In this case it is possible to easily detect especially defects which are not of point-like configuration, rather extend in the lengthwise direction of the material, in that the relevant signal lamp continuously lights-up.

Figure 3:
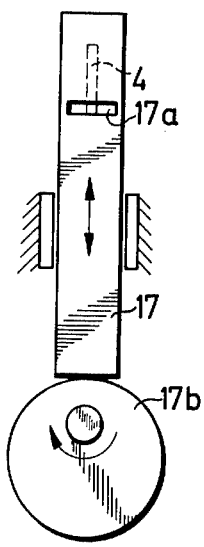
FIG. 3 is a view corresponding to the showing of FIG. 2, but illustrating a variation of a detail thereof.

In FIG. 3 there is illustrated a different possibility for interrupting the parallel bundle of light rays 4. A strip 17 formed of non-transparent material and located in the path of the rays is mounted to be displaceable parallel to the plane of the rays and perpendicular to the rays. It possesses a transparent slot 17a. The drive of the strip 17 occurs through the agency of an eccentric disk 17b which in turn is driven by a not particularly illustrated motor. The eccentricity of the disk and thus the stroke of the strip 17 are calculated such that the slot 17a periodically migrates to-and-fro from one to the other edge of the bundle or beam of light rays. With this arrangement the surface of the material web is continuously impinged or scanned. With suitable electrical construction of the indicator device it is however possible to divide the entire width of the material web into individual partial regions and to again associate therewith a respective signal lamp.

An apparatus of the previously described type was used for controlling the freshly poured layer of a lithographic film having a web width of 110 centimeters. As the light source there was used a He-Ne-laser of 1mW output power, the rays of which were fanned out by the cylindrical lens system into a parallel bundle of rays of a cross-section of $4 \times 40$ mm$^2$. The angle of incidence of the laser beam at the film surface amounted to 3°. There was used a circular disk diaphragm of the type shown in FIG. 2 and having eight slots. The disk was driven by a synchronous motor at 50 revolutions per second. The indicator device embodied eight signal lamps which were arranged over the corresponding regions over the film web.

The inventive apparatus for the detection of errors has two considerable advantages. Firstly, it only requires relatively small optical components and with the exception of the moved diaphragm possesses no mechanically moved components. Due to the foregoing it is constructionally extremely simple and functionally reliable. Such factors and the small size of the optical components —simple lenses of conventional diameter— are extremely favorable from the standpoint of the fabrication costs of the apparatus.

Although the inventive apparatus under consideration has been described as a matter of convenience in conjunction with the checking and control of photographic materials, it is to be of course understood that the apparatus is also suitable for determining surface defects or flaws of other reflecting material webs, for instance metal-, glass- or plastic plates and foils, trickle films flowing over supports, free-falling liquid curtains or liquid films produced by extrusion. Similarly, also the combination of a laser light source with a cylindrical optical system and a movable diaphragm is not only very advantageous for the detection of surface defect locations, rather generally for scanning purposes of all types.

While there is shown and described present preferred embodiments of the invention, it is to be distinctly understood that the invention is not limited thereto, but may be otherwise variously embodied and practiced within the scope of the following claims. ACCORDINGLY,

What is claimed is:

1. An apparatus for detecting defect locations at the surface of a moved reflecting material, comprising a light source, a first optical system which directs the light emanating from said light source successively at surface regions of the material located along a line extending essentially transversely with respect to the direction of movement of the material, a photoelectric transducer and a second optical system which collects the light reflected from individual surface regions of the material at the transducer, an indicator device which as a function of the intensity of the light reflected from each surface region generates a signal corresponding to the relevant surface region, the improvement comprising said light source consisting of a laser light source, said first optical system splitting up the laser beam into an essentially two-dimensional parallel bundle of light rays, the plane of which approximately perpendicularly intersects the surface of the material to be inspected and which two-dimensional parallel bundle of light rays grazingly impinges upon the material surface at a predetermined angle of incidence, and a movable diaphragm arranged in the path of the light rays impinging upon the material, said diaphragm periodically only freeing individual partial regions of the planar bundle of light rays.

2. The apparatus as defined in claim 1, wherein the signal which is generated is an optical signal.

3. The apparatus as defined in claim 1, wherein said predetermined angle is smaller than 5°.

4. The apparatus as defined in claim 3, further including a non-transparent obstacle arranged in the path of light rays between the second optical system and the photoelectric transducer in such a manner that the light rays reflected at the predetermined angle of incidence are collected at the obstacle and light rays reflected at an angle different than the predetermined angle of incidence are deflected past the obstacle and collected at the photoelectric transducer, and wherein the indicator device only then generates a signal when the photoelectric transducer has been illuminated by the light rays deflected past the obstacle.

5. The apparatus as defined in claim 1, wherein the indicator device controls a number of signal generators each of which is operatively associated with a certain position of the diaphragm.

6. The apparatus as defined in claim 5, wherein the signals generated by the indicator device last approximately for the duration of the period of the diaphragm movement.

7. The apparatus as defined in claim 1, wherein the movable diaphragm consists of a disk which is rotatable about an axis arranged essentially parallel to the direction of the light rays and externally thereof, said disk possessing a series of substantially arcuate-shaped slots of the same central angle but different radii.

8. The apparatus as defined in claim 1, wherein the movable diaphragm possesses a slot, and means for continuously moving said slot to-and-fro parallel to the plane of the bundle of light rays but transversely to the direction of the rays.

9. The apparatus as defined in claim 1, wherein the wavelength of the laser light is in the longwave visible range of the spectrum.

10. The apparatus as defined in claim 1, wherein the wavelength of the laser light is in the near infrared range.

* * * * *